United States Patent [19]
Washizuka

[11] Patent Number: 5,541,416
[45] Date of Patent: Jul. 30, 1996

[54] ESTIMATION METHOD AND APPARATUS FOR SEMICONDUCTOR LIGHT EMITTING ELEMENT CAPABLE OF INSPECTING BY WAFER

[75] Inventor: Syoichi Washizuka, Yokohama, Japan

[73] Assignee: Kabushiki Kaisha Toshiba, Kawasaki, Japan

[21] Appl. No.: 285,533

[22] Filed: Aug. 4, 1994

[30] Foreign Application Priority Data

Aug. 6, 1993 [JP] Japan ................................. 5-196419

[51] Int. Cl.⁶ ........................... G01N 21/64; G01R 31/26
[52] U.S. Cl. ..................................... 250/458.1; 250/459.1
[58] Field of Search .............................. 250/458.1, 459.1

[56] References Cited

U.S. PATENT DOCUMENTS

| | | | |
|---|---|---|---|
| 5,227,638 | 7/1993 | Mizushima et al. | 250/458.1 X |
| 5,381,016 | 1/1995 | Moriya | 250/458.1 |

FOREIGN PATENT DOCUMENTS 2-268254  11/1990  Japan ................................. 250/458.1

OTHER PUBLICATIONS

Black et al., "Scanned–Laser Microscope For Photoluminescence Studies", Applied Optics, vol. 11, No. 7, Jul. 1972, pp. 1553–1562.

Upton et al., "Fluorescence Quantum Yield Determination by Pulsed Source Single Photon Counting", Analytical Chemistry, vol. 51, No. 12, Oct. 1979, pp. 1941–1945.

Primary Examiner—Carolyn E. Fields
Assistant Examiner—Edward J. Glick
Attorney, Agent, or Firm—Oblon, Spivak, McClelland, Maier & Neustadt, P.C.

[57] ABSTRACT

A luminous efficiency is estimated by obtaining a life time a of few carriers controlling the luminous efficiency. An estimation method inadiates pulsed laser light for exciting carriers in a light emitting layer by a co-focal point optical system, at a specified position of the light emitting layer of a light emitting element formed on a surface of a wafer. A life time is obtained by detecting the fluorescent light emitted from the specified position in the light emitting layer corresponding to an irradiation of the pulsed laser light and by observing a change of the fluorescent light with lapse of a time. A luminous efficiency is estimated at the specified position in the light emitting layer from the life time on the basis of a correlation of a life time and a luminous efficiency previously obtained, thereby enabling an estimation of the light emitting element at a wafer stage without destroying the wafer and without contact therewith.

5 Claims, 6 Drawing Sheets

ESTIMATION METHOD AND APPARATUS FOR SEMICONDUCTOR LIGHT EMITTING ELEMENT CAPABLE OF INSPECTING BY WAFER

BACKGROUND OF THE INVENTION

1. Field of the Invention

The present invention relates to an inspection apparatus for inspecting electric and luminous characteristics of semiconductor light emitting elements such as a light emitting diode (LED), a laser diode and the like, and more specifically relates to an estimation apparatus for a semiconductor light emitting element capable of inspecting the light emitting element as a wafer before attaching electrodes and the like.

2. Discussion of the Background

While manufacturing a semiconductor device by using a semiconductor wafer, it is necessary to select wafers by previously investigating the characteristics of the wafers. Unless the determination is properly done as to whether wafers have defects or not, yield and reliability decrease to result in an increase in manufacturing cost. In the same manner, it is necessary to judge the quality of elements and to properly select the elements on the basis of a characteristic value which is investigated from each of the elements after a plurality of elements are formed on the semiconductor wafer. Especially, since the application of a LED recently extends to not only a single lamp but also to an array and a display panel, the LED pellets having higher quality are required in large quantities.

In a conventional epitaxial wafer for the LED, after the wafer on which elements are previously formed is divided into a plurality of pellets, electric and luminous characteristics are investigated by a sampling inspection. Particularly, it is widely performed that a pellet is selected in accordance with the luminous efficiency.

However, it is difficult for the conventional method to combine shortening a time spent on a work and an improvement of an inspection accuracy. Namely, since a sampling number is limited from the viewpoint of shortening a time, an inspection accuracy decreases, thereby resulting in that evenness between the selected pellets can not be obtained in a good reproduction. In the case of the light emitting diode, a discrepancy of characteristics in a wafer surface and between wafers becomes large at each lot, and the reappearance is insufficient. As a result, there is a luminance discrepancy in a screen of the completed display. On the contrary, since the sampling number should increase for improving an accuracy, an inspection time becomes longer.

Therefore, there is provided a selection method at a wafer stage before dividing the wafer into a plurality of pellets. This method is a practical application of a die sort method which is used for manufacturing an integrated circuit (IC). When the die sort method applies to an LED, an electric division between elements is not performed at the wafer stage in the LED, and for example, after electrodes of each of the elements are formed, the elements are divided by performing a half die in which the wafer is attached to an adhesive sheet and a groove is cut on the wafer. Each of the elements is sequentially scanned to drive a light emission, and a luminous efficiency is measured on the basis of a light detection level. However, scattering between adjacent pellets can not be avoided even though the elements are divided, thereby resulting in a problem that a correct measured value can not be obtained. As a result of an actual attempt, it is impossible to obtain an accuracy sufficient to the extent capable of withstanding a practical use because there many discrepancies against a measured value after dividing the wafer into a plurality of pellets. Furthermore, since a scar of a probe remains by any methods, it is easy for an unevenness of a bonding strength in the latter bonding step to result.

SUMMARY OF THE INVENTION

An object of the present invention is to provide an estimation method and apparatus of a semiconductor light emitting element capable of estimating the elements without destroying the elements and without contact therewith at a wafer stage before electrodes are formed on the elements and without a reception of an influence of a mutual interference caused by a scattering between the adjacent pellets.

In order to achieve the above objective, an estimation apparatus for a semiconductor light emitting element according to a first aspect of the present invention comprises pulsed laser light generation means for generating a pulsed laser light for exciting carriers in a light emitting layer formed on a wafer so as to generate a fluorescent light, a co-focal point optical system for introducing the pulsed laser light into a first focal point and for introducing into a second focal point only light emitted from the first focal point, a position determination means for positioning the first focal point in the light emitting layer, a photodetector means provided at the second focal point for detecting the fluorescent light in the light emitting layer reflecting an irradiation of the pulsed laser light, a waveform analyzing means for obtaining a life time from a damped waveform of the fluorescent light after observing the fluorescent light with a lapse of time, and an estimation means for estimating a luminous efficiency in the light emitting layer corresponding to the life time obtained by the waveform analyzing means on the basis of a correlative relationship between a predetermined life time and a luminous efficiency.

An estimation apparatus for a semiconductor light emitting element according to a second aspect of the present invention comprises pulsed laser light generation means for generating a pulsed laser light for exciting carriers in a light emitting layer of a plurality of light emitted elements arranged in two-dimensions on a wafer so as to generate a fluorescent light, a co-focal point optical system for introducing the pulsed laser light into a first focal point and for introducing into a second focal point only light emitted from the first focal point, a depth direction scanning means for scanning a position of the first focal point in the depth direction of the light emitting elements, an element arrangement scanning means for scanning the position of the first focal point along an arrangement of the plurality of the light emitting elements, a photodetector means provided at the second focal point for detecting the fluorescent light in the light emitting layer reflecting an irradiation of the pulsed laser light, a waveform analyzing means for obtaining a life time from a damped waveform of the fluorescent light after observing the fluorescent light at each of the light emitting elements with a lapse of time, and an estimation means for estimating a luminous efficiency in the light emitting layer of each of the light emitting elements corresponding to the life time obtained by the waveform analyzing means on the basis of a correlative relationship between a predetermined life time and a luminous efficiency.

An estimation method according to a third aspect of the present invention comprises the steps of irradiating a pulsed laser light for exciting carriers in a light emitting layer by using a co-focal point optical system at a specified position in the light emitting layer of a light emitting element formed on an upper surface of a wafer, detecting a fluorescent light generated from the specified position in the light emitting layer corresponding to an irradiation of the pulsed laser light, obtaining a life time of the fluorescent light after observing the fluorescent light with a lapse of a time, and estimating a light emitting efficiency at the specified position in the light emitting layer from the life time on the basis of a correlative relationship of a predetermined life time and light emitting efficiency.

The present invention operates from a viewpoint that light having an energy larger than and sufficient to approximate the energy of a forbidden band of a semiconductor has a comparatively large invading distance into the semiconductor. The present invention obtains a life time of a small number of carriers deciding a light emitting efficiency without destroying the semiconductor and without contact therewith by measuring a time attenuation of a luminous occurring by irradiating the pulsed laser light from the upper surface into an activation layer of the wafer. Accordingly, the apparatus of the present invention generates the pulsed laser light, focuses a focal point in the activation layer by the co-focal point optical system having a pinhole filter, selectively detects a fluorescent light from the focal point in generated fluorescent light, sequentially scans positions of the focal point in the activation layer and elements on the wafer, and estimates a luminous efficiency of the light emitting elements from a distribution of the depth of time attenuation of the fluorescent light.

As described above, since the apparatus of the present invention obtains the life time of the carriers from the attenuation time constant of the luminous waveform of the inner fluorescent light of the measured elements and estimates the luminous efficiency of the measured elements on the basis of the depth distribution of the life time without destroying the measured elements and without contact therewith, it is unnecessary to provide steps of attaching electrodes and dividing elements, thereby eliminating an influence of the correlative interference caused by scattering and absorption of light between adjacent elements. Accordingly, it is possible to perform an element estimation on the wafer stage as a step previous to the conventional estimation step, thereby improving an inspection efficiency and a throughput.

Furthermore, since a plurality of light emitting elements are sequentially changed one by one as a measured object, it is possible to automatically measure a plurality of the elements on the semiconductor wafer, thereby improving a throughput from this viewpoint. Accordingly, it is possible to utilize an inspection of entire elements on the wafer in a short time, to prevent a defective wafer and defective elements flowing to the next step, and to select a grade at the wafer stage on the basis of a luminous efficiency, thereby contributing an improvement of a quality control of a wafer and an improvement of a productivity.

Moreover, mapping of a luminous efficiency in a wafer causes a reliability of a die sort to increase, and an accuracy of ranking of a luminous largely improves, thereby largely decreasing a luminous discrepancy in a surface and occurring at a manufacturing step of an array and display, and improving a yield of manufacturing. In this manner, the present invention can result in a large improvement by an industrial use and has an extremely high practical value.

DETAILED DESCRIPTION OF THE PREFERRED EMBODIMENTS

There will now be described in detail an estimation apparatus and method for a semiconductor light emitting element according to preferred embodiments of the present invention in reference with the attached drawings.

Figure 1:
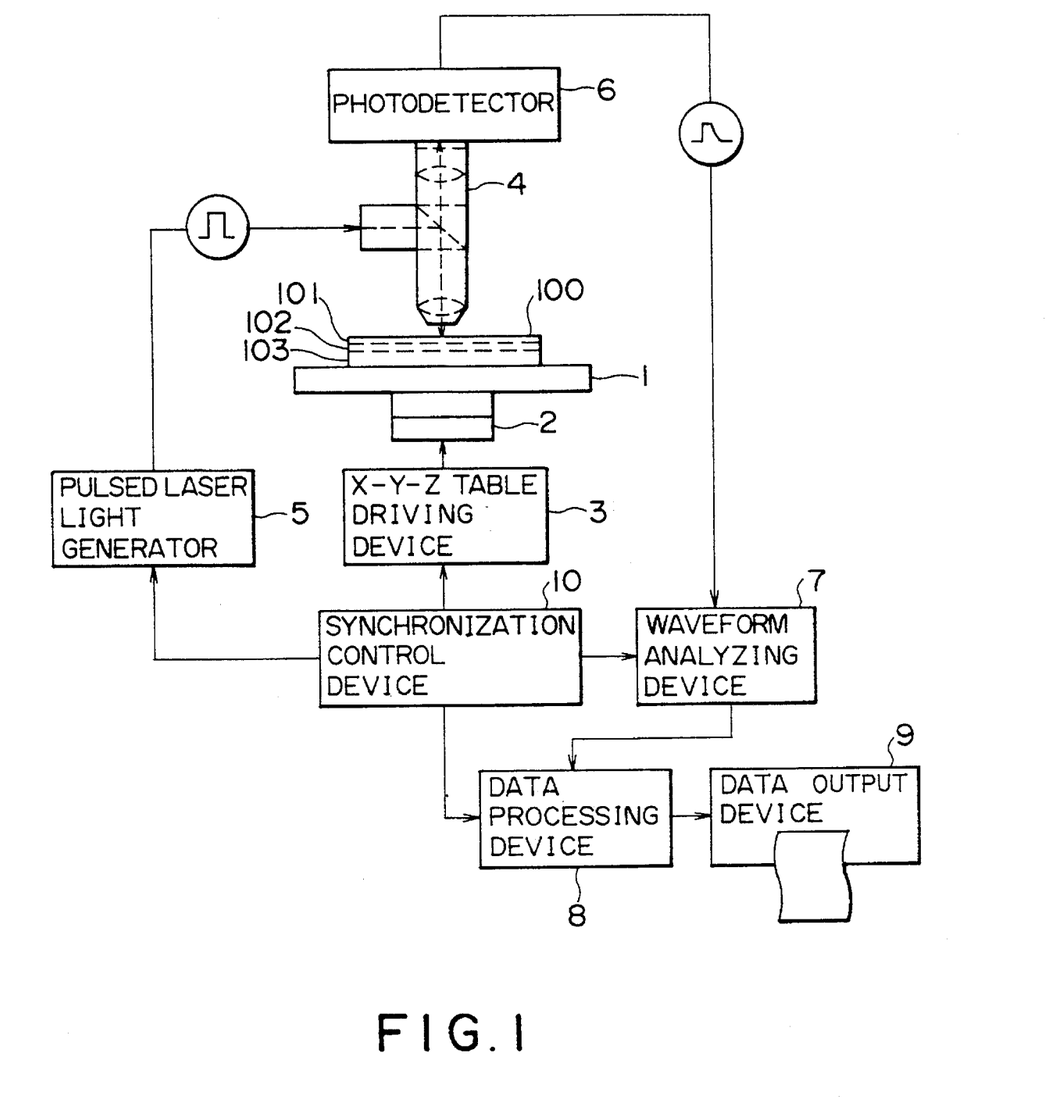
FIG. 1 is a block diagram showing a constitution, of an estimation apparatus for a semiconductor light emitting element according to an embodiment of the present invention.

FIG. 1 shows a constitution of an estimation apparatus according to a first embodiment of the present invention. In FIG. 1, numeral 100 denotes a wafer having a surface on which a PN junction is formed over an entire region. The wafer 100 does not have electrodes for supplying an electric power and a cur groove for electrically dividing elements because it is unnecessary to form them. A light emitting layer 101 of a light emitting element is made from a P-layer, a light emitting layer 102 is an N-layer, and numeral 103 is a substrate. Numeral 1 denotes a measuring stage. The wafer 100 is put on the measuring stage 1. Numeral 2 denotes an X-Y-Z table on which the measuring stage 1 is mounted so as to freely move in an X-Y plane and the Z-axis direction. By this, the wafer 100 also freely moves. Numeral 3 denotes an X-Y-Z table driving device for driving the X-Y-Z table 2. The X-Y-Z table 2 and the X-Y-Z table driving device correspond to a position determination means, a depth direction scanning means and an element arrangement scanning means.

Numeral 4 denotes a co-focal point optical system having a pinhole filter for converging pulsed light from a pulsed laser light generator 5 as exited light generation means to irradiate into the wafer 100, thereby generating fluorescent light. Numeral 6 denotes a photodetector as a light detection means, 7 a waveform analyzing device as waveform analysis means, 8 a data processing device as an estimation means, and 9 a data output device. The photo-detector 6 receives the fluorescent light from the wafer 100 to perform a photo-electric conversion, thereby supplying an output signal to the waveform analyzing device 7.

Figure 5:
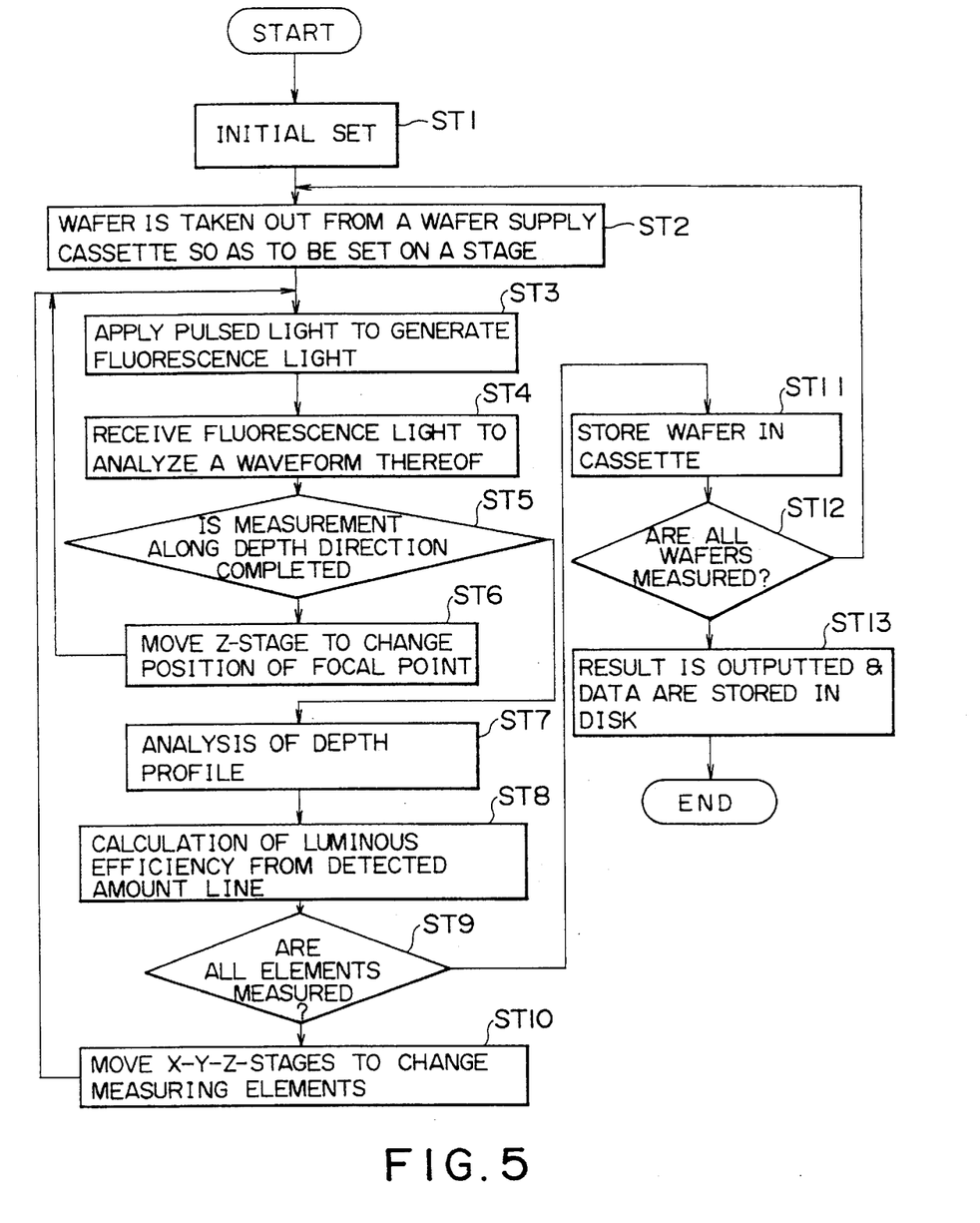
FIG. 5 is a flow chart showing a processing content of a data processing apparatus shown in FIG. 1.

The data processing device 8 has functions for obtaining a luminous efficiency of elements on the basis of life time data from the waveform analyzing device 7, for determining as to whether an objective element is an excellent article or not after comparing various luminous efficiencies such as a luminous efficiency at a predetermined depth, a luminous efficiency as a peak of a predetermined depth, and a distribution profile of luminous efficiencies in the depth direction with standard values or standard profile waveforms, and for determining a rank of the element on the basis of a magnitude of the luminous efficiency. Furthermore, the data processing device 8 also has a function for storing a plane distribution of the luminous efficiencies of a light emitting element group arranged on the wafer 100 to statistically process the distribution. As described in more detail, the device 8 executes processing as shown in FIG. 5, and controls the entire estimation work. An estimated result in the data processing device 8 is printed out by the data output device 9 according to various formats. A synchronization control device 10 controls a timing among a determination of the X-Y-Z position of the wafer 100, a supply of the pulsed laser light, and a reception of the measured data corresponding to a measurement indication signal of the data processing device 8. Even though a description is not given, the apparatus shown in FIG. 1 has means fop marking a district of the defective elements and the like.

Figure 2:
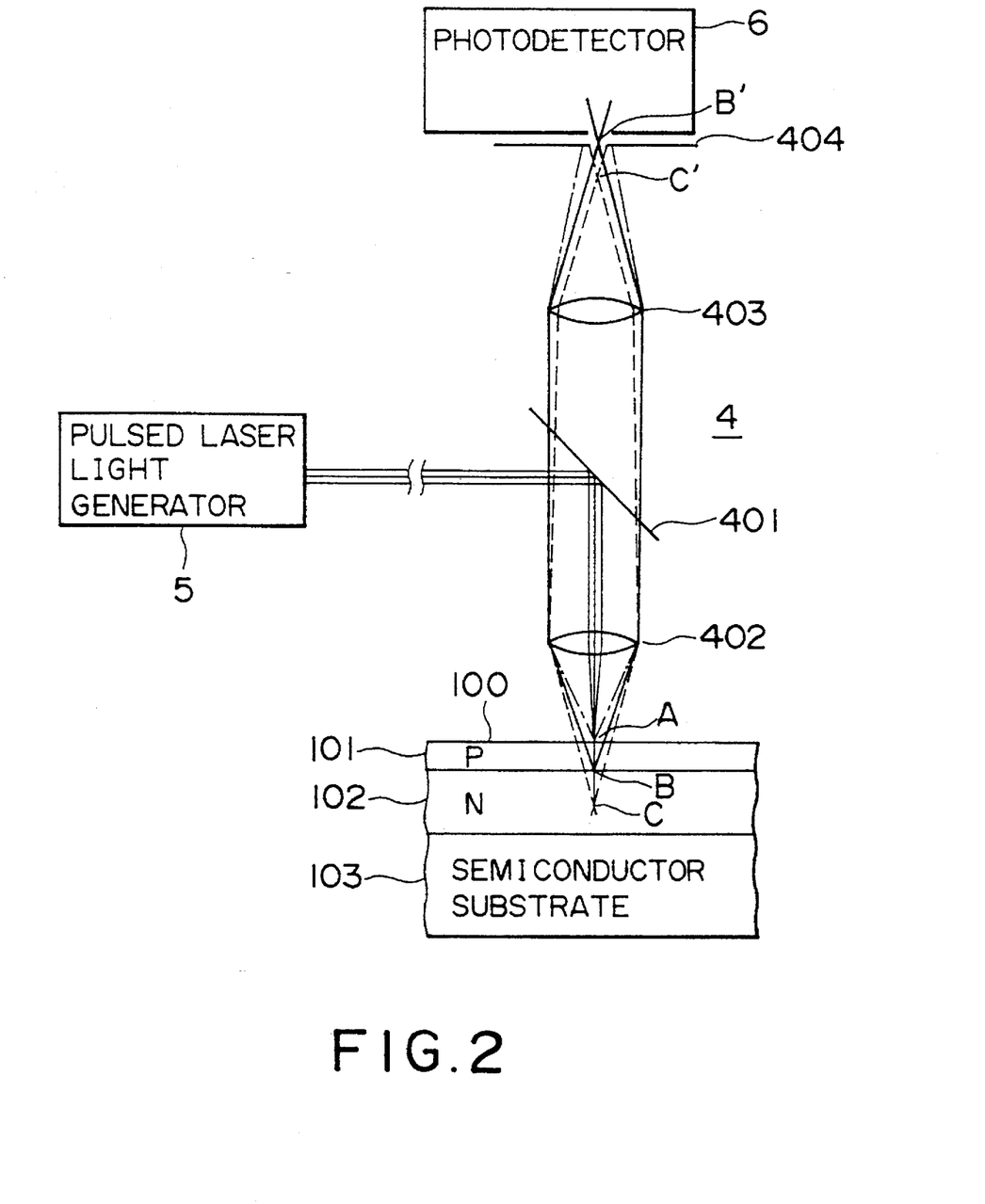
FIG. 2 is a diagram for explaining a detailed constitution and an operation principle of a co-focal point optical system as a component of the present invention.

FIG. 2 shows a detailed configuration of the co-focal point optical system 4. In FIG. 2, numeral 401 denotes a dichroic mirror for reflecting the irradiated pulsed light and for passing through the generated fluorescent light, and numeral 402 denotes a first converging (object) lens for converging light in a focal point B in the wafer 100. A fluorescent light generated by an irradiation of the pulsed light inversely passes through the first converging lens 402 and the dichroic mirror 401 and is converged again by a second converging (focusing) lens 403 to focus a focal point B'. A pinhole filter 404 is arranged on a focal point plane formed before the photodetector 6. A pinhole of the pinhole filter 404 causes the fluorescent light generated from the focal point B to pass through without an interruption to effectively irradiate the light into the photodetector 6. However, the pinhole interrupts the majority of the fluorescent light generated from positions A and C except the focal point B because they are converged on A' (not shown) and C' without a part which can reach the photodetector 6. However, the above manner, it is possible to selectively detect the fluorescent light from the focal point B by means of the co-focal point optical system 4. The co-focal point 4 can be diverted from a microscope including a co-focal point optical system. Even though the conventional co-focal point optical system observes a surface condition of a semi-transparent material and a semi-transparent sample having a strong scattering, the present invention can selectively observe an internal fluorescent light generated from a transparent material.

Figure 3:
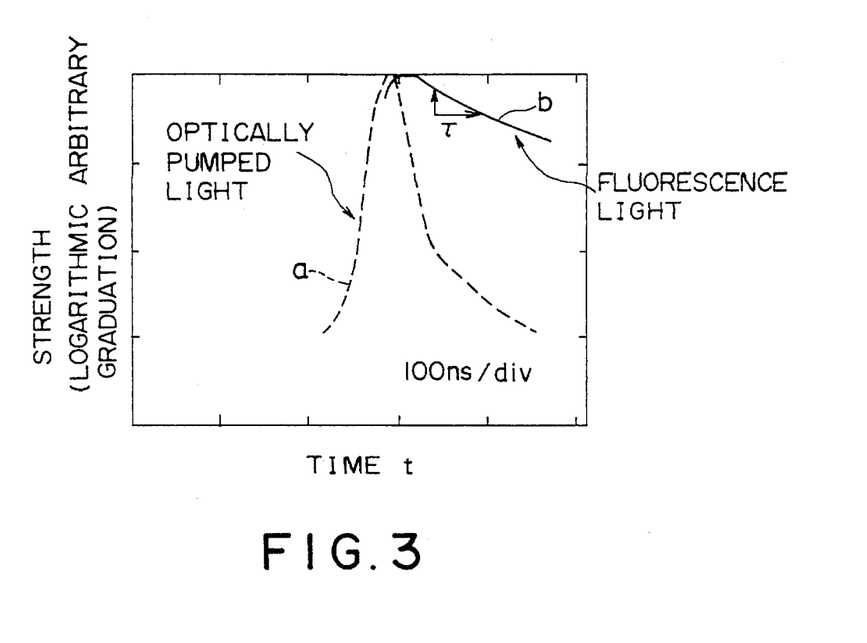
FIG. 3 is a waveform diagram showing an example of a detection signal of a pulsed light irradiating into a measured object element and a fluorescent light generated from the measured object element.

FIG. 3 shows an example of a detection output of the photodetector 6. In FIG. 3, a dotted line a shows a waveform of the pulsed laser light irradiated into the wafer 100, and a solid line b shows an example of the light detection waveform (response) of the fluorescent light generated by the pulsed laser light. The waveform analyzing device 7 approximates an attenuation waveform of the output signal of the photodetector 6 by an index function to obtain an attenuation time constant by means of a method of a least square. The time constant shows a life time of carriers. For example, it is possible to use "$I(t)=I_0 \times \exp(-t/\tau)$" as the index function. In this equation, symbol $I_0$ is a peak value of the fluorescent light, $\tau$ is the attenuation time constant, and t is a time. The attenuation time constant $\tau$ is obtained by an approximation. Here, even though the peak value $I_0$ receives an influence of an adsorption and scattering, it is noted that the constant $\tau$ does not receive the influence at all. The time constant $\tau$, namely, life time, has a closely correlative relationship with the luminous efficiency as described later.

Figure 4:
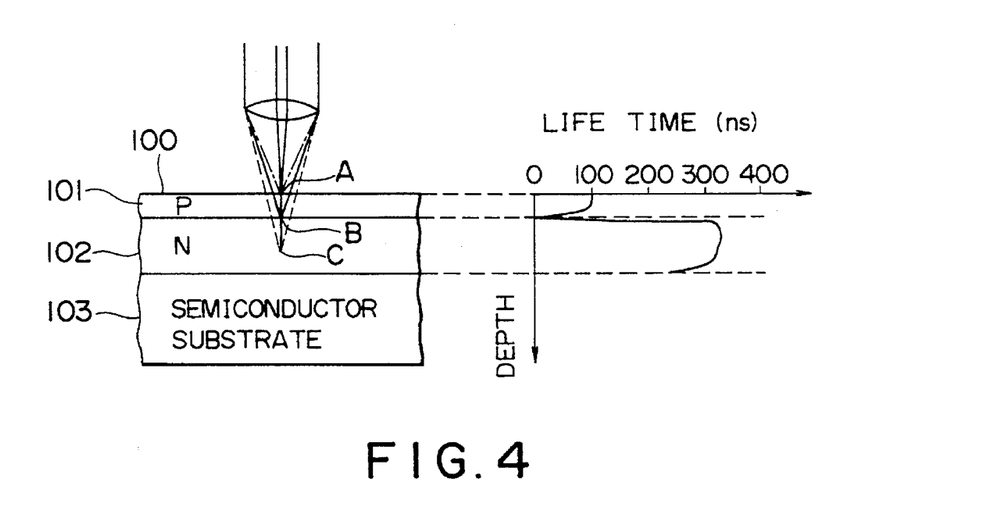
FIG. 4 is a diagram showing an example of a depth profile of a life time from a surface of a wafer of the measured object element.
Figure 6:
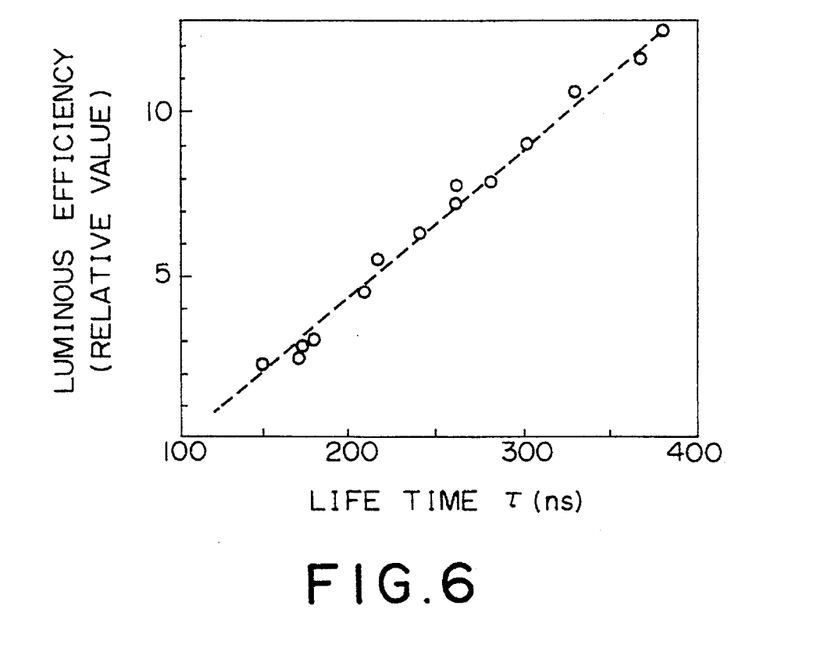
FIG. 6 is a diagram showing a correlation between a life time and a luminous efficiency.

FIG. 4 shows a typical example of the distribution in the depth direction of the life time of the wafer 100 on which the light emitting elements are formed. In the example shown in FIG. 4, there is a distribution that the life time is smaller in the P-layer 101 and larger in the N-layer 102. Accordingly, if the life time is sequentially measured by moving the position of one focal point of the co-focal point optical system from A to C in the depth direction of the wafer 100, it is possible to obtain the distribution of the life time in the depth direction shown in FIG. 4. The life time can be changed into a distribution of a luminous efficiency in the depth direction on the basis of the correlation of the life time and luminous efficiency which is previously obtained in the depth direction as shown in FIG. 6.

Next, there is described an outline of a measurement and data processing in reference with FIG. 5.

In step ST1, an initial set is first performed. Here, a kind and caliber of the wafer and a measurement mode or the like are set. The kind of the wafer includes an ID (identification code) of a kind such as a kind of the elements which are formed on the wafer, for example, an LED having a red emission as a luminous color, and an LED having a green emission as a luminous color, and is referred at a selection of a standard value which is compared and contrasted with the measured data in an estimation described later. The caliber is a diameter of the wafer and is referred to for indicating a driving stroke through the synchronization control device 10 to the X-Y-Z driving table 3 when the elements are positioned one by one on the X-Y-Z table 2. The measurement mode indicates a mode for measuring all of the elements or a mode for measuring a part of the elements. When the measurement mode is the mode for measuring a part of the elements, the measurement mode functions as an indication of a pitch for measuring at every several elements.

After the initial set, a set of the wafer 100 onto the measuring stage 1 is indicated to a not shown wafer delivering device in step ST2. By this, one wafer 100 is extracted from a wafer supply cassette (not shown) so as to set it on the measuring stage 1. After an alignment of the wafer 100 (positioning in the X, Y and Z directions), a measuring preparation is completed, thereby issuing a work completion message from the wafer delivering device. Then, a measurement stars. Here, one focal point on one objective side is determined on a surface of the wafer in the same manner as a fluorescent measurement.

In step ST3, an irradiation of the pulsed laser light to the wafer 100 generates a fluorescent light.

In step ST4, the pinhole filter 404, which is arranged on the other focal point on the image side of the co-focal point optical system 4, selectively detects only fluorescent light occurring from the focal point on the objective side, thereby taking it into the waveform analyzing device 7 through the photodetector 8. Then, a life time is obtained for showing an attenuation time constant of the fluorescent light waveform. In step ST5 it is judged whether or not a measurement of the life time distribution in the depth direction of the wafer 100 is completed. If the measurement is not completed, the Z stage is moved in step ST6, thereby lifting the Z stage in the manner that the focal point position is set in the wafer 100 (the X and Y stages are not moved). A moving amount $\Delta Z$ is set to an equation of "ΔZ=d/n" in accordance with an optical principle, where d is a depth of the focal point under the surface of the wafer 100, and n is a refractive index of the wafer 100. Steps ST3–ST6 are repeated until the measurement of the life time distribution in the depth direction is completed. When the measurement is completed, the data processing device 8 analyzes a depth profile of the life time in step ST7, for example, the depth position and the maximum value of the life time are obtained as quality estimation parameters. In step ST8, a luminous efficiency showing the life time data obtained at step ST7 is obtained by a detected amount line as shown by a dotted line in FIG. 6. The detected amount line shows a correlation between a life time and luminous efficiency of a small number of carriers, and is preset in the data processing device 8 after adopting data by an actual measurement. A simple method of presetting is to adopt a table and to calculate intermediate values by interpolation. By this, the apparatus ends the measurement of the luminous efficiency of one light emitting element. The measured luminous efficiency is compared with a reference value of a luminous efficiency of a lot which is set previously. As a result of the comparison, a proper marking may be attached to the light emitting element which is judged as the rejected article. Alternatively, the data processing device stores a position of the rejected light emitting element on the wafer. The measured data of each light emitting element are stored in the data processing device 8 with the position on the wafer. It is possible to use as a quality estimation parameter various comparison references such as a peak and depth position of the life time (luminous efficiency), a life time of a specified depth, a shape and slant of a distribution curve in the depth direction of the life time, and a position of the peak or bottom. In step ST9, a judgement is performed as to whether all of the elements have been measured or not. If all of the elements have not been measured, the X-Y stages are moved to a position of the next element, and at the same time, the Z stage moves to fall down in the manner of returning the focal point on the surface of the wafer 100. Steps ST3–ST10 are repeated until measurements for all of the elements are completed.

When all of the elements have been measured, the wafer delivering device (not shown) returns the wafer 100 to a storage cassette (not shown) at step ST11. After that, at step ST12, a judgement is performed as to whether the measurement of all of the wafers is completed or not. If the measurement is not completed, the operation returns to the step ST2. Namely, steps ST2–ST12 are repeated until the measurement on all the wafers is completed. When the measurement of all the wafers is completed, a processing result is printed out by the data output device 9 at step ST13. Alternatively, the processing result may be displayed on a cathode ray tube (CRT) monitor which is not shown in the figures.

According to the present embodiment, since the life time shown by the attenuation time constant in the fluorescent light waveform of the measured element is obtained for an estimation of the luminous efficiency of the measured element on the basis of the depth profile in the light emitting layer, it is unnecessary to provide manufacturing steps of attaching electrodes to the measured elements and dividing elements of the wafer, thereby eliminating an influence of a mutual interference caused by an adsorption and scattering of light between adjacent pellets. Further, it is possible to estimate an element characteristic in the wafer stage with a high accuracy, thereby improving throughput. Moreover, even though the life time near the PN junction dominates the luminous efficiency in the light emitting element, the conventional method of the fluorescent light measurement only obtains the life time near the surface of the wafer 100. Since the life time on the surface easily receives an influence of the surface condition (defect, distortion and damage) and is not a main light emitting region, a correlation may be wrong between the measured data and the luminous efficiency. On the contrary, since the present embodiment can obtain the life time of the main light emitting region without destroying the measured element and without contact therewith, the correlation between the luminous efficiency becomes better, thereby enabling an estimation in the inner condition of the light emitting element.

Next, there is described a result with respect to an inspection by using a system constitution of the embodiment shown in FIG. 1. A sampled element is an epitaxial wafer for a green LED formed on a GaP wafer. A cassette (25 plates) of the epitaxial wafers having a diameter of 5.08 cm (2 inches) is prepared to perform a measurement according to the procedure shown in FIG. 5 with respect to the light emitting elements of two thousands per one wafer by 1 mm of pitch. In this connection, energy of a forbidden band of GaP is about 2.34 eV (about 530 nm) at a room temperature, a refractive index is about 3.5, and an adsorption coefficient of light is about $10^3$ cm$^{-1}$. Accordingly, a degree of 520–530 nm is proper for the wavelength of the pulsed light irradiated for obtaining an internal fluorescent light having a light loss as small as possible. At this time, 30 % of the irradiated light is reflected on the surface of the wafer 100, and the remaining 70 % of light permeates into the wafer 100. A degree of 26 % of the permeated light is attenuated, and is further attenuated to about 10 % under 20 μm under the surface.

Since a thickness of the P-layer 101 is usually about 10 μm, it is possible to sufficiently excite the fluorescent light across the PN junction to the N-layer 102. On the other hand, even though an occurring light is further fine, since the adsorption coefficient is inversely and sufficiently small, the fluorescent light can be taken out of the wafer 100.

A result is typically shown in FIG. 4, and the depth profile of the life time is 70–120 ns in the P-layer 101. The depth profile once falls down and increases to 200–350 ns in the N-layer 102. As described above, the life time of the N-layer has a strong correlation with the luminous efficiency. For example, the correlation thereof is shown in FIG. 6. Furthermore, this is the same as the life time of the luminous efficiency obtained by the pulsed laser light flowing in the light emitting element.

Figure 7:
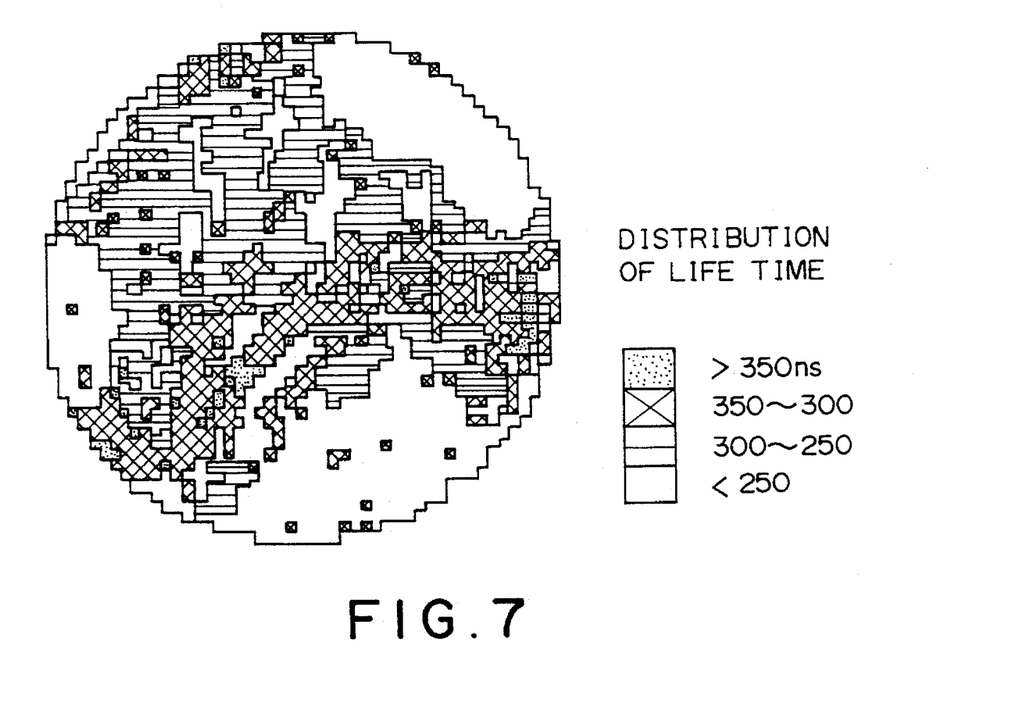
FIG. 7 is a diagram showing map data when the apparatus of the present invention measures a distribution of the life time in a surface of the wafer.

FIG. 7 shows an example of a distribution in a plane of the wafer 100. Three portions which are regions having a large life time can be found in the wafer, and FIG. 7 shows a three times objective distribution of (111) wafer.

Figure 8:
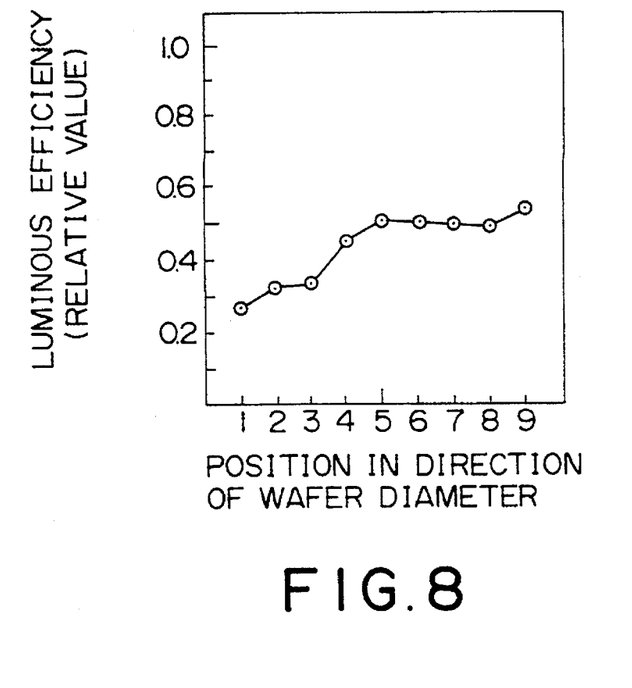
FIG. 8 is a diagram showing a correspondence between a distribution of the element luminous efficiency in the direction of the wafer diameter and a distribution in the diameter direction of a life time.

FIG. 8 shows a distribution of the luminous efficiency in the diameter direction of the wafer after completing the LED as a final article. The distribution shown in FIG.8 properly coincides with the result which is previously obtained by FIG. 7.

In the case where the apparatus according to the present invention is used, the measurement with all LEDs of 2000 articles by 25 wafers is completed within a predetermined time which is a limit for processing 20 articles per one wafer in the conventional method. Accordingly, it is possible to measure the light emitting elements precisely with an improvement of 1000 percent in comparison with the conventional method, thereby resulting in high speed processing with several seconds of the measuring time per one measuring point. As described above, the present invention can obtain an accurate measuring result and a precise estimation result in a short time. In this embodiment, the measurement is performed by the luminous efficiency in the place of the life time as shown in FIG. 6. When the measured result by the present embodiment with respect to 20 LEDs on the wafers is compared with the measured result by the conventional method with respect to 20 LEDs, they coincide with each other within a range of ±5 %. This number is a small number of errors at a degree of which an artisan can not find what measuring method is used for the measurement.

In order to utilize the present invention, it is desired that the pulsed laser light source 5 applies a dye laser excited by a strong pulse exciting light source such as a nitrogen ($N_2$) laser. It is also desired that the photodetector 6 may have a response speed in a degree of watching the life time, and be generally comprised of a photomultiplier, PIN photodiode, avalanche photodiode (APD) and streak camera. A photon counting method is suitable for properly detecting a fine fluorescent light.

Figure 9:
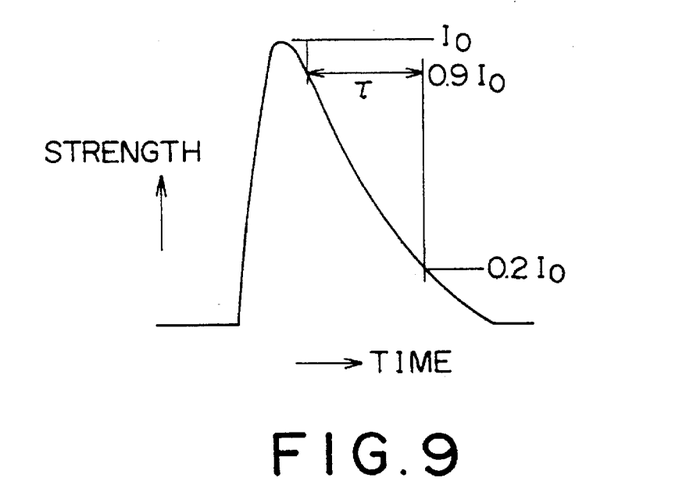
FIG. 9 is a diagram showing an approximation for obtaining a life time of a fluorescent light occurring from the measured object.

Furthermore, even though the above described embodiment approximates the attenuation waveform of the fluorescent light to the index function and obtains the time constant by means of the method of least squares, the present invention may adopt an approximation for obtaining a time until attenuating from $0.9I_O$ to $0.2I_O$ as shown in FIG. 9.

Moreover, when the other embodiment adopts a light emitting element having a cladding layer of an energy larger than the energy of a forbidden band in the activation layer such as an AlGaAs high luminance LED, an InGaAlP four elements high luminance orange-green LED and the like, it is possible to obtain the same effect by a high sensitivity more than an amount that an adsorption in the cladding layer sharply decreases. Accordingly, by applying the present invention to the other embodiment, there is a large merit that it is possible to obtain the characteristics of the activation layer without a destructive estimation in which the cladding layer is removed by an etching such as in the conventional method.

In the above-mentioned embodiments, even though the apparatus selects the pulsed light having energy as near as possible to an energy of the forbidden band of the activation layer to obtain the depth profile of the life time, the present invention may use together a method of changing an invading distance into the wafer 100 by sequentially changing energy of the pulsed laser light. Namely, this method operates that, when energy of the pulsed laser light is caused to be higher, an adsorption in the wafer increases sharply, thereby disabling to obtain the fluorescent light in the region deeper than the region that the adsorption increased.

Furthermore, the apparatus of the present invention may comprise a spectroscope (not shown) after the pinhole filter 404 to further implement a method of obtaining a waveform spectrum of the fluorescent light.

Still furthermore, the apparatus of the present invention may be provided for not only a luminance selection of the light emitting elements but also a luminance ranking of the wafer 100. In this case, since a luminance is satisfied by an average value within a region broader than the value of each element, it is possible to judge a trend of the entire wafer by measuring as few points as possible. Therefore, it is possible to control a quality of the wafer by early monitoring in the middle of the wafer manufacturing step.

Moreover, the P-layer 101 may apply to the wafer formed by an impurity diffusion. Namely, if the life time of the region (depth of 5µm) at which the PN junction is formed is previously obtained, the luminous efficiency is also predicted. Furthermore, it is possible to obtain a merit for enabling an optimization of process checking and process parameters by monitoring a diffusion step on the basis of the change of the life time before and after the diffusion step.

As described above, the apparatus according to the present invention can utilize various modifications within a scope which does not deviate from the subject matter of the present invention.

What is claimed is:

1. An estimation apparatus for a semiconductor light emitting element, comprising:

pulsed laser light generation means for generating pulsed laser light for generating fluorescent light by exciting carriers in a light emitting layer of a light emitting element formed on a wafer;

a co-focal point optical system for introducing said pulsed laser light to a first focal point of co-focal points and for introducing to a second focal point of the co-focal points only light emitted from said first focal point;

position determination means for determining a position of said first focal point in said light emitting layer;

photodetector means provided at said second focal point for detecting said fluorescent light in said light emitting layer in response to irradiation of said pulsed laser light;

waveform analyzing means for obtaining a life time of said fluorescent light based on an attenuation waveform after an observation of said fluorescent light with a lapse of time; and estimation means for estimating a luminous efficiency in said light emitting layer corresponding to said life time obtained by said waveform analyzing means based on a correlation of life time and luminous efficiency, said correlation being previously predetermined.

2. The estimation apparatus according to claim 1, wherein said estimation means estimates said luminous efficiency based on a distribution profile of said life time in a depth direction from a surface of said light emitting element.

3. An estimation apparatus for a semiconductor light emitting element, comprising:

pulsed laser light generation means for generating pulsed laser light for generating fluorescent light by exciting carriers in a light emitting layer of a plurality of light emitting elements which are arranged in two dimensions on a wafer;

a co-focal point optical system for introducing said pulsed laser light to a first focal point of co-focal points and for introducing to a second focal point of the co-focal points only light emitted from said first focal point;

depth direction scanning means for scanning a position of said first focal point in a depth direction of said light emitting elements;

element alignment scanning means for scanning a position of said first focal point along an alignment of said plurality of light emitting elements;

photodetector means provided at said second focal point for detecting said fluorescent light in response to irradiation of said pulsed laser light;

waveform analyzing means for obtaining a life time of said fluorescent light based on an attenuation waveform after an observation of said fluorescent light with a lapse of time; and estimation means for estimating a luminous efficiency in said light emitting layer corresponding to said life time obtained by said waveform analyzing means based on a correlation of life time and luminous efficiency, said correlation being previously predetermined.

4. The estimation apparatus according to claim 3, wherein said estimation means estimates said luminous efficiency based on a distribution profile of said life time in the depth direction from a surface of said light emitting elements.

5. An estimation method for a semiconductor light emitting element, comprising:

a step of irradiating pulsed laser light for generating fluorescent light by exciting carriers in a light emitting layer by means of a co-focal point optical system, at a specified position in said light emitting layer of a light emitting element formed on a surface of a wafer;

a step of obtaining a life time of said fluorescent light by detecting said fluorescent light emitted from said specified position in said light emitting layer corresponding to irradiation of said pulsed laser light and by observing a change of said fluorescent light with a lapse of time; and a step of estimating a luminous efficiency at said specified position of said light emitting layer from said life time based on a correlation of life time and luminous efficiency which is previously predetermined.

* * * * *